(12) United States Patent
Cheng

(10) Patent No.: US 11,950,945 B2
(45) Date of Patent: Apr. 9, 2024

(54) RADIOGRAPHY DIAGNOSIS DEVICE

(71) Applicant: NanoRay Biotech Co., Ltd., Taipei (TW)

(72) Inventor: Wen-Yuan Cheng, Taipei (TW)

(73) Assignee: NanoRay Biotech Co., Ltd., Taipei (TW)

( * ) Notice: Subject to any disclaimer, the term of this patent is extended or adjusted under 35 U.S.C. 154(b) by 259 days.

(21) Appl. No.: 17/499,885

(22) Filed: Oct. 13, 2021

(65) Prior Publication Data

US 2022/0142595 A1    May 12, 2022

Related U.S. Application Data

(60) Provisional application No. 63/110,371, filed on Nov. 6, 2020.

(30) Foreign Application Priority Data

Aug. 25, 2021    (TW) .................................. 110131451

(51) Int. Cl.
*A61B 6/06*    (2006.01)
*A61B 6/00*    (2006.01)
(Continued)

(52) U.S. Cl.
CPC .............. *A61B 6/4405* (2013.01); *A61B 6/06* (2013.01); *A61B 6/107* (2013.01); *A61B 6/4085* (2013.01);
(Continued)

(58) Field of Classification Search
None
See application file for complete search history.

(56) References Cited

U.S. PATENT DOCUMENTS 4,646,338 A * 2/1987 Skillicorn ................ H05G 1/32
378/102
7,142,638 B2   11/2006 Polichar et al.
(Continued)

FOREIGN PATENT DOCUMENTS

CN         2706130        6/2005
CN      204092005 U  *   1/2015
(Continued)

OTHER PUBLICATIONS

"Office Action of Taiwan Counterpart Application", dated Oct. 28, 2021, p. 1-p. 3.
(Continued)

*Primary Examiner* — Thomas R Artman
(74) *Attorney, Agent, or Firm* — JCIPRNET

(57) ABSTRACT

A radiography diagnosis device includes a casing having an opening, a first shielding structure, a dose measuring unit, a transmission-type X-ray source module, and an image receiving assembly. The first shielding structure is disposed in the casing and forms a shielded space located between the transmission-type X-ray source module and the image receiving assembly and corresponding to the opening. An object to be detected is adapted to enter the shielded space through the opening. The transmission-type X-ray source module is disposed in the casing and adapted to provide an X-ray toward the object to be detected in the shielded space. The image receiving assembly is disposed in the casing. During image capturing, the X-ray generated by the transmission-type X-ray source module is received by the dose measuring unit, and the image receiving assembly receives the X-ray passing through the object to be detected at the same time.

11 Claims, 5 Drawing Sheets

(51) Int. Cl.
  *A61B 6/08* (2006.01)
  *A61B 6/10* (2006.01)
  *A61B 6/40* (2024.01)
  *A61B 6/42* (2024.01)
  *A61B 6/46* (2024.01)
  *A61B 6/50* (2024.01)

(52) U.S. Cl.
  CPC ............... *A61B 6/42* (2013.01); *A61B 6/461* (2013.01); *A61B 6/08* (2013.01); *A61B 6/505* (2013.01)

(56) References Cited

U.S. PATENT DOCUMENTS

| | | | | |
|---|---|---|---|---|
| 9,044,186 | B2* | 6/2015 | Ma | A61B 6/482 |
| 9,211,100 | B2* | 12/2015 | Ma | A61B 6/563 |
| 9,700,270 | B2* | 7/2017 | Tateishi | A61B 6/44 |
| 10,182,785 | B2* | 1/2019 | Daum | A61B 6/032 |
| 10,695,016 | B2* | 6/2020 | Lai | A61B 6/4405 |
| 10,736,599 | B2* | 8/2020 | Daum | A61B 6/032 |
| 10,898,148 | B2* | 1/2021 | Taneda | A61B 6/4283 |
| 2005/0276379 | A1* | 12/2005 | Polichar | G01T 1/2914 378/98.2 |
| 2013/0343519 | A1 | 12/2013 | Ma | |
| 2013/0345543 | A1* | 12/2013 | Steibel, Jr. | A61M 21/02 600/407 |
| 2015/0230765 | A1* | 8/2015 | Ma | A61B 6/508 378/62 |
| 2016/0135766 | A1* | 5/2016 | Tateishi | A61B 6/4266 250/370.09 |
| 2016/0296197 | A1* | 10/2016 | Daum | A61B 6/10 |
| 2017/0238892 | A1* | 8/2017 | Taneda | A61B 6/467 |
| 2019/0150873 | A1* | 5/2019 | Daum | A61B 6/032 |
| 2019/0246996 | A1* | 8/2019 | Lai | A61B 6/4452 |
| 2022/0142595 | A1* | 5/2022 | Cheng | A61B 6/461 |
| 2022/0148712 | A1* | 5/2022 | Cheng | A61B 6/107 |

FOREIGN PATENT DOCUMENTS

| | | | |
|---|---|---|---|
| CN | 108742671 | | 11/2018 |
| CN | 209032403 | | 6/2019 |
| CN | 209032404 | | 6/2019 |
| CN | 110680372 | | 1/2020 |
| CN | 113425317 A | * | 9/2021 |
| TW | 201350088 | | 12/2013 |
| TW | I652044 | | 3/2019 |

OTHER PUBLICATIONS

"Search Report of Europe Counterpart Application", dated Mar. 18, 2022, p. 1-p. 11.

* cited by examiner

RADIOGRAPHY DIAGNOSIS DEVICE

CROSS-REFERENCE TO RELATED APPLICATION

This application claims the priority benefits of U.S. provisional application Ser. No. 63/110,371, filed on Nov. 6, 2020 and Taiwanese application no. 110131451, filed on Aug. 25, 2021. The entirety of each of the above-mentioned patent applications is hereby incorporated by reference herein and made a part of this specification.

BACKGROUND

Technical Field

The disclosure relates to a radiography diagnosis device. Particularly, the disclosure relates to a functional radiography diagnosis device for a single diagnosis part.

Description of Related Art

A radiological diagnosis system diagnoses a human body through radiological images obtained by irradiating the human body with X-rays. For example, an X-ray diagnosis system for hands may perform diagnoses such as bone age detection for children, bone fracture diagnosis, rapid bone density screening, and gout detection. Generally, in the current radiological diagnosis system for hands, an X-ray source device, an X-ray irradiation zone, an image receiving device, and the like are separately disposed. As such, the overall system may not be moved easily and may be relatively space-occupying in a medical facility.

SUMMARY

The disclosure provides a radiography diagnosis device, which is easily movable and occupies less space.

The radiography diagnosis device of the disclosure includes a casing, a first shielding structure, a transmission-type X-ray source module, and an image receiving assembly. The casing has an opening. The first shielding structure is disposed in the casing and forms a shielded space. The shielded space corresponds to the opening. An object to be detected is adapted to enter the shielded space through the opening. The transmission-type X-ray source module is disposed in the casing and adapted to provide an X-ray toward the object to be detected in the shielded space. The image receiving assembly is disposed in the casing. The shielded space is located between the transmission-type X-ray source module and the image receiving assembly. During image capturing, the X-ray generated by the transmission-type X-ray source module is received by a dose measuring unit, and the image receiving assembly receives the X-ray passing through the object to be detected at the same time.

In an embodiment of the disclosure, the radiography diagnosis device further includes a shutter assembly. The shutter assembly is disposed in the casing and located between the transmission-type X-ray source module and the shielded space. The shutter assembly is adapted to control a duration of irradiation of the X-ray to the shielded space. The shutter assembly is adapted to limit a light-emitting angle range of the X-ray.

In an embodiment of the disclosure, the radiography diagnosis device further includes an image capturing device. The image capturing device is disposed in the casing and corresponds to the shielded space. The image capturing device is adapted to capture an image of the object to be detected in the shielded space.

In an embodiment of the disclosure, the radiography diagnosis device further includes an electric transmission interface. The electric transmission interface is disposed on the casing. The radiography diagnosis device is adapted to receive power and transmit data through the electric transmission interface.

In an embodiment of the disclosure, the radiography diagnosis device further includes a display interface. The display interface is disposed on the casing and is adapted to display an image received by the image receiving assembly.

In an embodiment of the disclosure, the casing has a transparent part. The transparent part corresponds to the shielded space. The object to be detected in the shielded space is adapted to be observed through the transparent part.

In an embodiment of the disclosure, a material of the transparent part includes a shielding material.

In an embodiment of the disclosure, the radiography diagnosis device further includes a dose measuring unit. The dose measuring unit is disposed in the casing and is adjacent to the shielded space. The dose measuring unit is adapted to measure a dose of the X-ray.

In an embodiment of the disclosure, the radiography diagnosis device further includes a second shielding structure. The second shielding structure is disposed in the casing and covers the transmission-type X-ray source module.

In an embodiment of the disclosure, a bottom edge of the casing has at least one finger-receiving groove, which facilitates transporting or moving the diagnosis device.

In an embodiment of the disclosure, the casing has a light-emitting part. The light-emitting part is adapted to emit at least two color lights. The color lights correspond to different operating states of the radiography diagnosis device.

In an embodiment of the disclosure, the casing has an emergency stop button part.

Based on the foregoing, in the disclosure, the first shielding structure, the transmission-type X-ray source module, and the image receiving assembly are integrated into the same casing, different from the general radiography diagnosis system in which the X-ray source device, the X-ray irradiation zone, and the image receiving device are separately disposed. Accordingly, the radiography diagnosis device of the disclosure is easily movable and occupies less space. Further, since the transmission-type X-ray source module of the disclosure has a greater light-emitting angle range than a reflection-type X-ray source, an overly long irradiation distance is not necessary for a sufficiently large irradiation area to be provided. Thereby, the distance between the transmission-type X-ray source module and the image receiving assembly (i.e., the source image distance (SID) as generally referred to) can be reduced, with the general capturing distance (the SID) for a hand reduced from 100 cm to 45 cm. Moreover, the transmission-type X-ray source module of the disclosure has a lower wattage, and accordingly a smaller size, than the reflection-type X-ray source. Therefore, in the disclosure, the miniaturization of the overall device volume is facilitated by using the transmission-type X-ray source module.

To make the aforementioned more comprehensible, several embodiments accompanied with drawings are described in detail as follows.

BRIEF DESCRIPTION OF THE DRAWINGS

The accompanying drawings are included to provide a further understanding of the disclosure, and are incorporated in and constitute a part of this specification. The drawings illustrate exemplary embodiments of the disclosure and, together with the description, serve to explain the principles of the disclosure.

DESCRIPTION OF THE EMBODIMENTS

Figure 1:
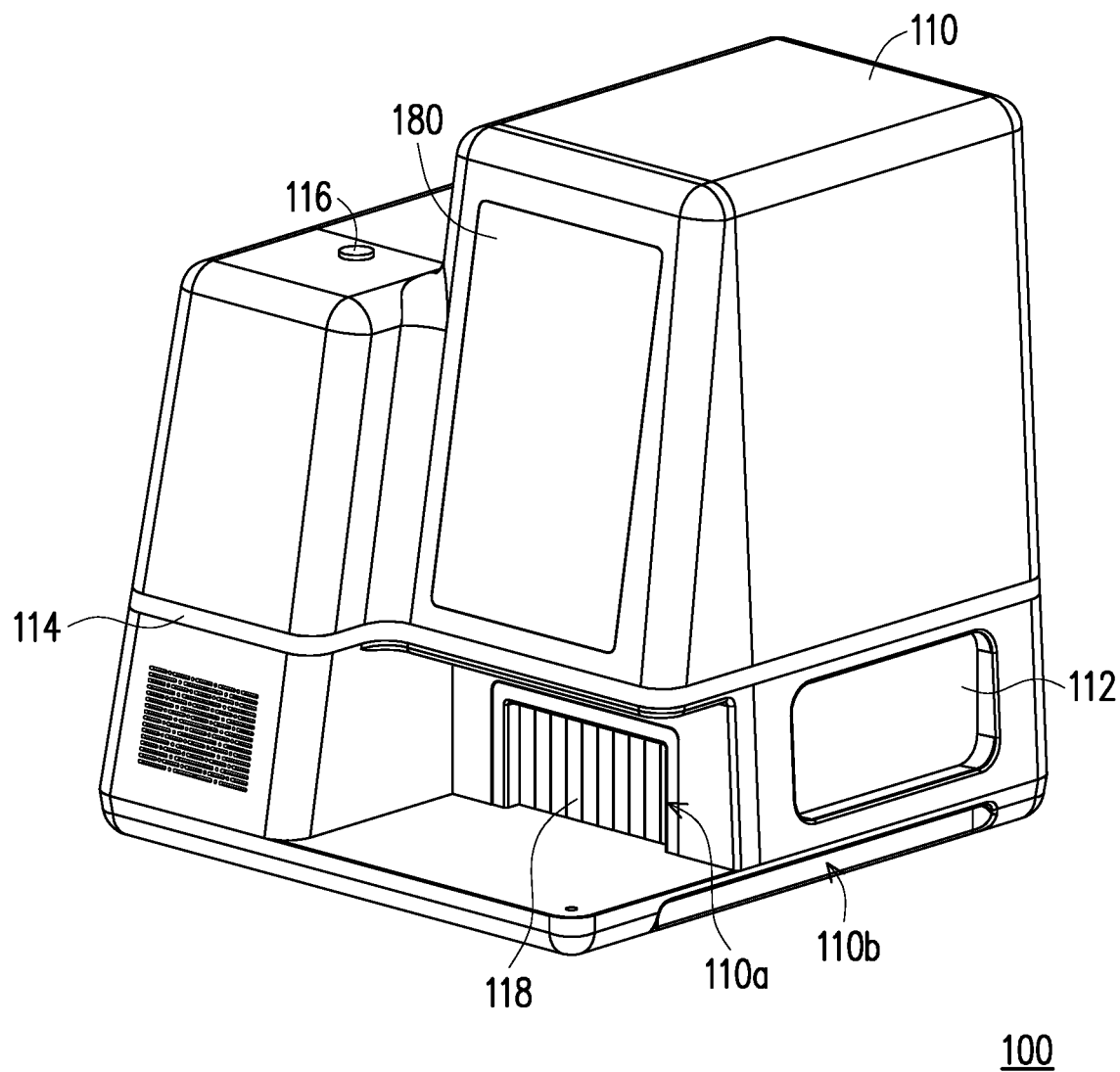
FIG. 1 is a perspective view of a radiography diagnosis device according to an embodiment of the disclosure.
Figure 2:
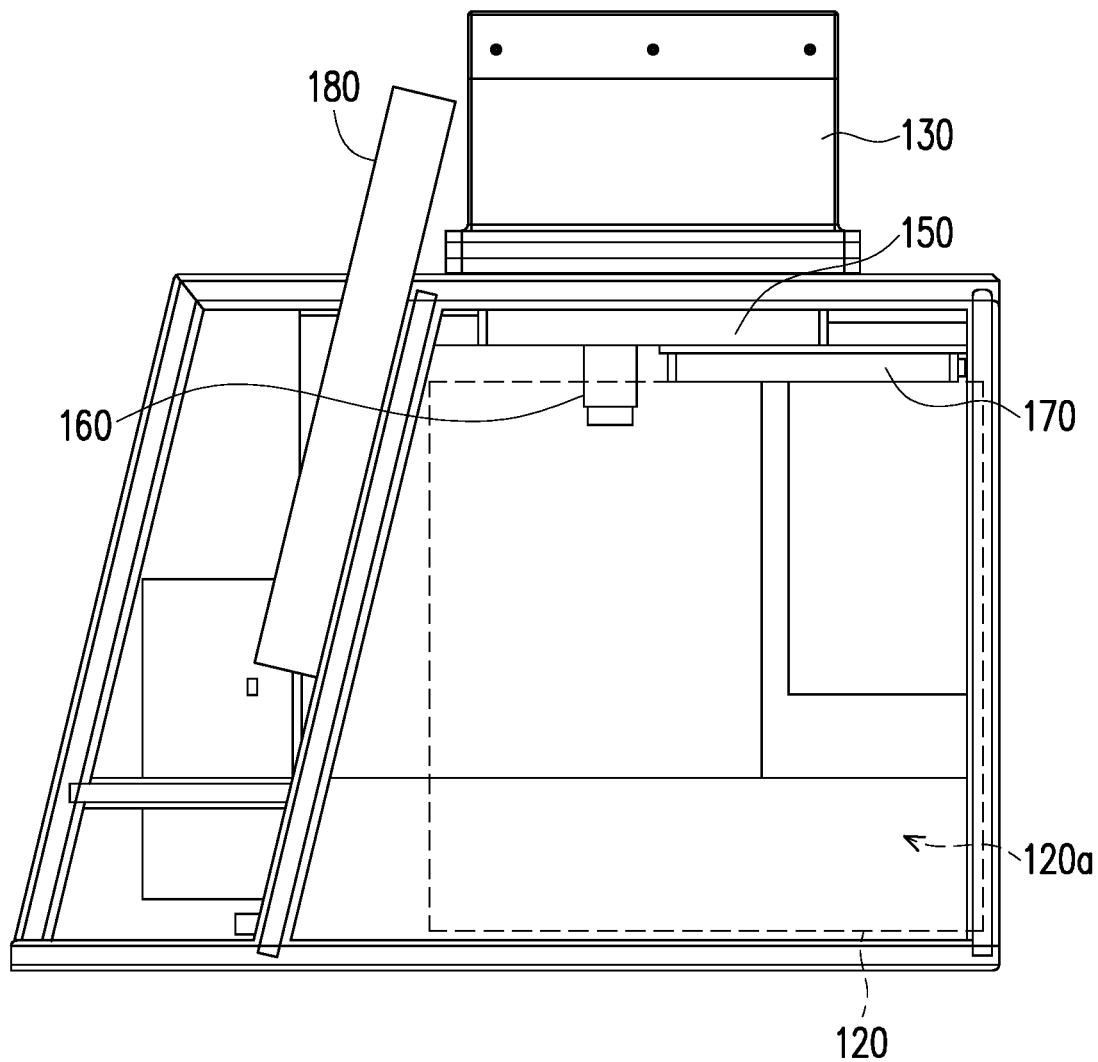
FIG. 2 is a side view of partial structures of the radiography diagnosis device of FIG. 1.
Figure 3:
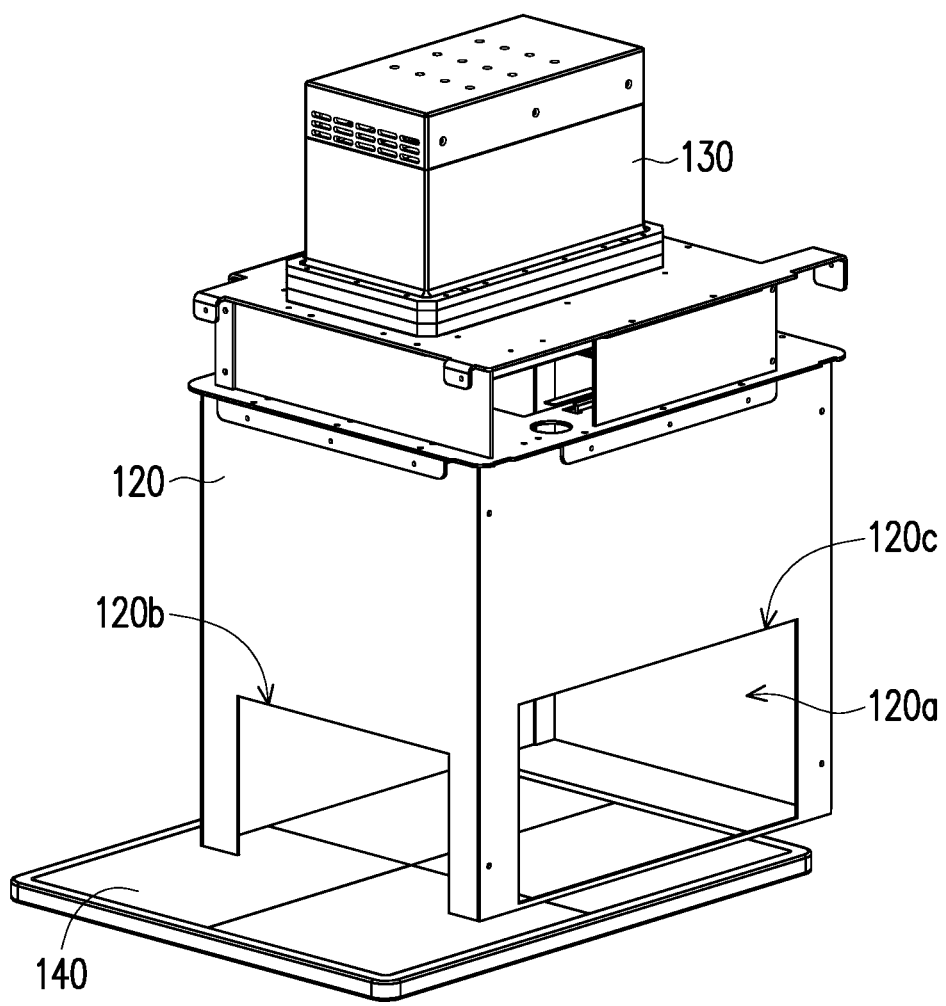
FIG. 3 is a perspective view of some members of the radiography diagnosis device of FIG. 1.

FIG. 1 is a perspective view of a radiography diagnosis device according to an embodiment of the disclosure. FIG. 2 is a side view of partial structures of the radiography diagnosis device of FIG. 1. FIG. 3 is a perspective view of some members of the radiography diagnosis device of FIG. 1. With reference to FIG. 1 to FIG. 3, a radiography diagnosis device 100 of this embodiment includes a casing 110, a first shielding structure 120, a transmission-type X-ray source module 130, and an image receiving assembly 140. The casing 110 has an opening 110a. The first shielding structure 120 is disposed in the casing 110 and forms a shielded space 120a corresponding to the opening 110a. The first shielding structure 120 has a recess opening 120b corresponding to the opening 110a. The transmission-type X-ray source module 130 is, for example, a transmission-type X-ray tube and is disposed in the casing 110. The image receiving assembly 140 is, for example, a flat panel detector (FPD) and is disposed in the casing 110. The shielded space 120a is located between the transmission-type X-ray source module 130 and the image receiving assembly 140.

Following the above, a hand of an object to be detected is adapted to enter the shielded space 120a of the first shielding structure 120 through the opening 110a of the casing 110 and the recess opening 120b of the first shielding structure 120. The transmission-type X-ray source module 130 is adapted to provide an X-ray to the object to be detected in the shielded space 120a. The material of the first shielding structure 120 includes, for example, lead and prevents X-ray leakage. The image receiving assembly 140 is adapted to receive an X-ray passing through the object to be detected to obtain a diagnostic image.

As mentioned above, in this embodiment, the first shielding structure 120, the transmission-type X-ray source module 130, and the image receiving assembly 140 are integrated into the same casing 110, different from the general radiography diagnosis system in which the X-ray source device, the X-ray irradiation zone, and the image receiving device are separately disposed. Accordingly, the radiography diagnosis device 100 of this embodiment is easily movable and occupies less space. Further, since the transmission-type X-ray source module 130 of this embodiment has a greater light-emitting angle range than a reflection-type X-ray source, an overly long irradiation distance is not necessary for a sufficiently large irradiation area to be provided. Thereby, the distance between the transmission-type X-ray source module 130 and the image receiving assembly 140 (i.e., the source image distance (SID) as generally referred to) can be reduced, with the general capturing distance (the SID) for a hand reduced from 100 cm to 45 cm. Moreover, the transmission-type X-ray source module 130 of this embodiment has a lower wattage, and accordingly a smaller size, than the reflection-type X-ray source. Therefore, in this embodiment, the miniaturization of the overall device volume is facilitated by using the transmission-type X-ray source module 130.

With reference to FIG. 2, the radiography diagnosis device 100 of this embodiment further includes a shutter assembly 150. The shutter assembly 150 is disposed in the casing 110 and located between the transmission-type X-ray source module 130 and the shielded space 120a. The transmission-type X-ray source module 130 is, for example, a continuous X-ray source. The shutter assembly 150 is configured to control a duration of irradiation of the X-ray from the transmission-type X-ray source module 130 to the shielded space 120a. In addition, the shutter assembly 150 may also be configured to limit the light-emitting angle range of the X-ray. The shutter assembly 150 has a smaller size than other types of mechanical/electronic beam collimators. Therefore, the miniaturization of the overall device volume is facilitated.

The radiography diagnosis device 100 of this embodiment, as shown in FIG. 2, further includes an image capturing device 160, which is disposed in the casing 110 and corresponds to the shielded space 120a of the first shielding structure 120. The image capturing device 160 is adapted to capture an image of the object to be detected in the shielded space 120a, such that a user may accordingly determine whether the object to be detected is in a correct position in the shielded space 120a. Specifically, the radiography diagnosis device 100 may be connected to other external electronic equipment (e.g., a computer), and display the image captured by the image capturing device 160 through the electronic equipment for the user to view. In addition, the position of the object to be detected in the shielded space 120a may be further determined by calibration software in the electronic equipment to accurately calibrate the position of the object to be detected. Moreover, the radiography diagnosis device 100 of this embodiment, as shown in FIG. 2, further includes a dose measuring unit 170, which is disposed in the casing 110 and is adjacent to the shielded space 120a of the first shielding structure 120. The dose measuring unit 170 is configured to measure a dose of the X-ray. Accordingly, the user knows whether the dose of the X-ray meets expectations.

With reference to FIG. 1, in this embodiment, the radiography diagnosis device 100 may include a display interface 180, which is a liquid crystal display panel or other types of display panels, for example. The display interface 180 is disposed on the casing 110 and is adapted to display the image received by the image receiving assembly 140. In other words, the image received by the image receiving assembly 140 may be displayed not only by the external electronic equipment, but also directly by the display interface 180 of the radiological diagnostic apparatus 100. In addition, the display interface 180 may also be configured to display other operating information of the diagnostic device 100. The display content thereof is not limited by the disclosure.

With reference to FIG. 1 and FIG. 3, in this embodiment, the casing 110 has a transparent part 112, and the first shielding structure 120 has an open slot 120c. The transparent part 112 corresponds to the shielded space 120a and the open slot 120c of the first shielding structure 120. The object to be detected in the shielded space 120a is adapted to be observed through the transparent part 112. Accordingly, the user may observe the hand (i.e., the object to be detected) reaching into the shielded space 120a through the transparent part 112, and a sense of fear of reaching the hand into the radiography diagnosis device 100 can be reduced. Thereby, the case where children are unwilling to take a radiological diagnosis by the radiography diagnosis device 100 can be greatly alleviated. In this embodiment, the material of the transparent part 112 includes a shielding material (e.g., lead) and prevents X-ray leakage. Specifically, the transparent part 112 is, for example, lead glass.

Figure 4:
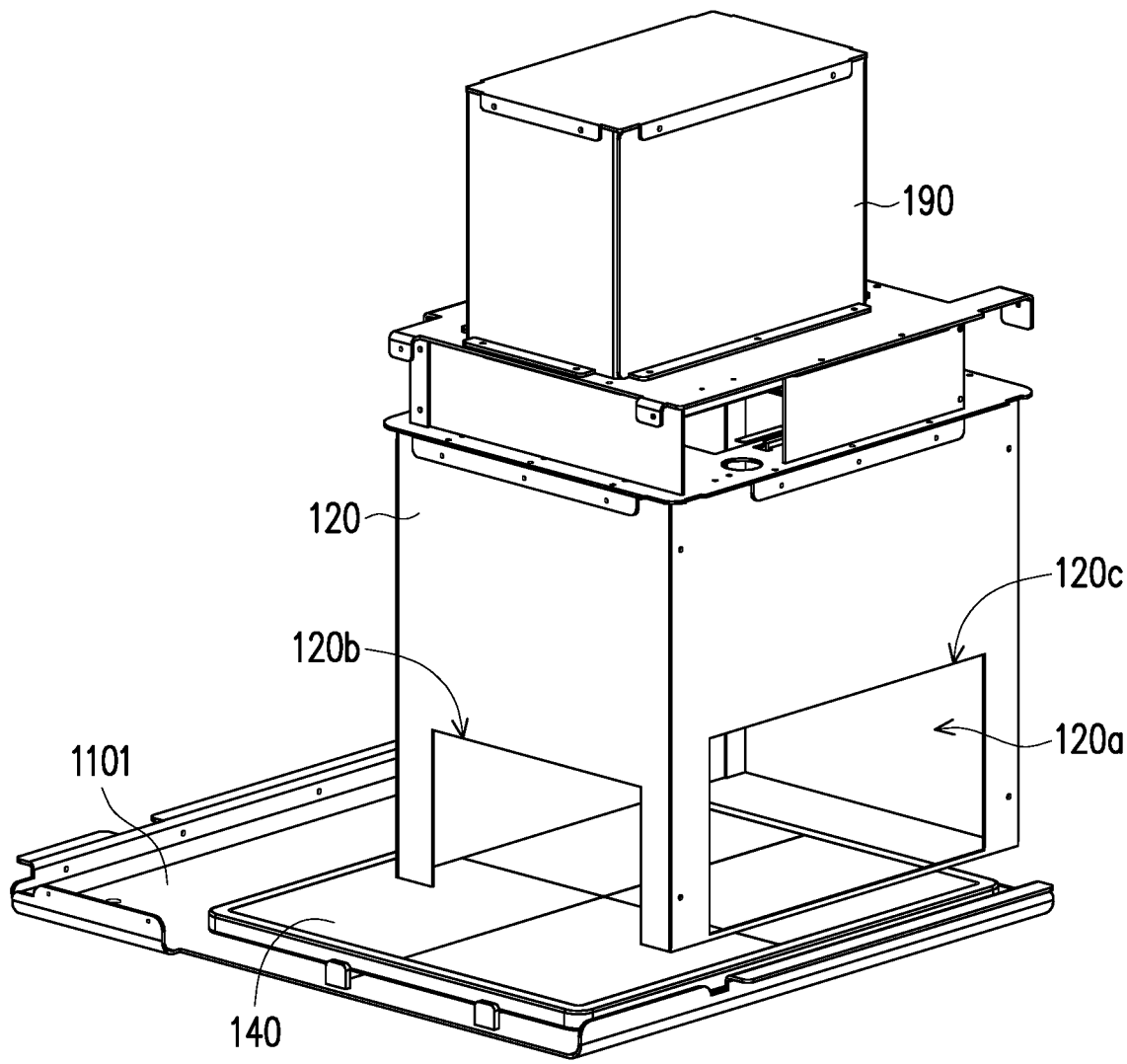
FIG. 4 is a perspective view of some members of the radiography diagnosis device of FIG. 1.

FIG. 4 is a perspective view of some members of the radiography diagnosis device of FIG. 1. With reference to FIG. 3 and FIG. 4, in this embodiment, the radiography diagnosis device 100 further includes a second shielding structure 190. The second shielding structure 190 is disposed in the casing 110 and covers the transmission-type X-ray source module 130. The material of the second shielding structure 190 includes, for example, lead and prevents X-ray leakage. In addition, as shown in FIG. 4, the image receiving assembly 140 is, for example, retractably mounted on a bottom plate 1101 in the casing 110 (shown in FIG. 1), such that the image receiving assembly 140 may be easily detached or replaced. In this embodiment, a shielding layer (e.g., a lead plate) may be disposed under the bottom plate 1101 to prevent X-ray leakage. Furthermore, as shown in FIG. 1, a shielding curtain 118 (e.g., a lead curtain) may be disposed at the opening 110a of the casing 110 to prevent X-ray leakage through the opening 110a.

Figure 5:
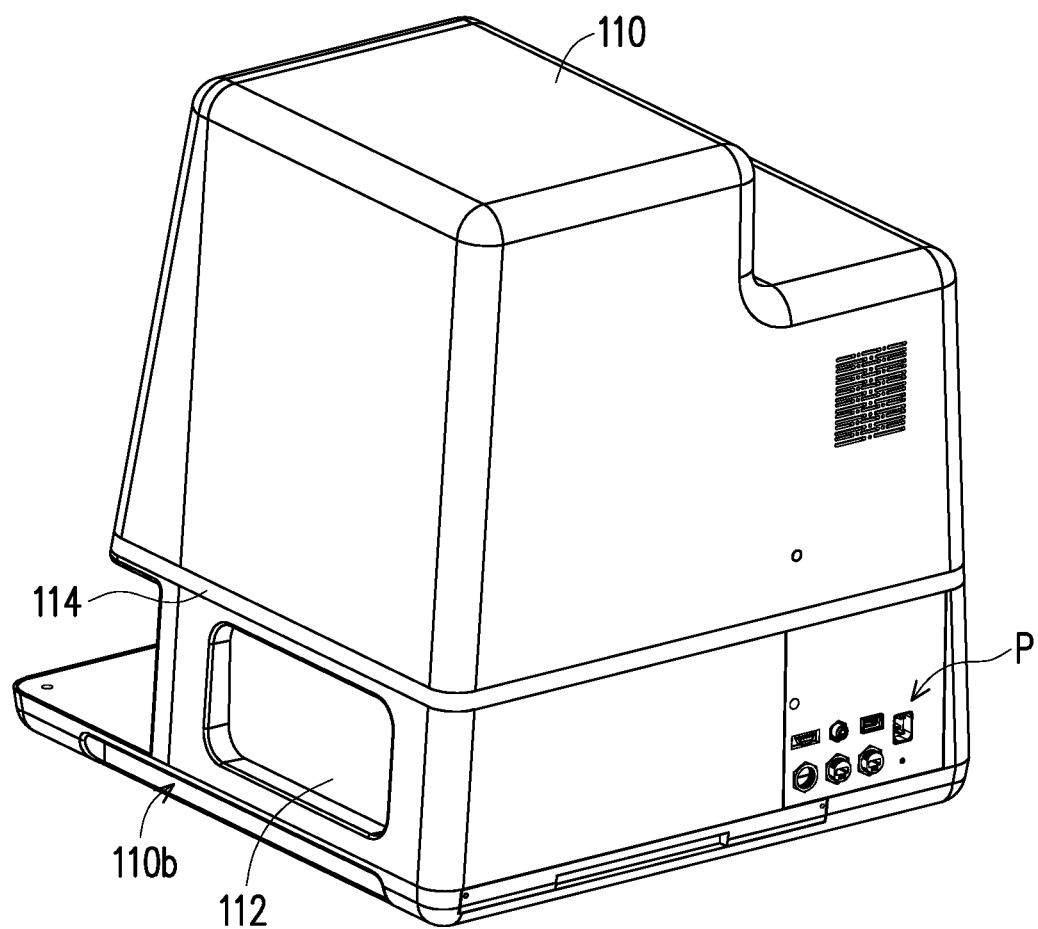
FIG. 5 is a perspective view of the radiography diagnosis device of FIG. 1 from another view angle.

FIG. 5 is a perspective view of the radiography diagnosis device of FIG. 1 from another view angle. With reference to FIG. 5, the radiography diagnosis device 100 of this embodiment further includes an electric transmission interface P. The electric transmission interface P is disposed on the casing 110. The radiography diagnosis device 100 is adapted to receive power and transmit data through the electric transmission interface P. For example, the external electronic equipment mentioned above may be connected to the radiography diagnosis device 100 through the electric transmission interface P. In addition, the radiography diagnosis device 100 may also be connected to an external controller through the electric transmission interface P to accordingly control the operation of the radiography diagnosis device 100. In other embodiments, the radiography diagnosis device 100 may also transmit and receive data signals in other appropriate manners (e.g., wireless transmission), which is not limited by the disclosure.

With reference to FIG. 1 and FIG. 5, in this embodiment, the bottom edge of the casing 110 has at least one finger-receiving groove 110b. When the user intends to move the radiography diagnosis device 100, the finger-receiving groove 110b is available for fingers of the user to reach in and apply force to easily move the radiography diagnosis device 100. In addition, the casing 110 of this embodiment has a light-emitting part 114. The light-emitting part 114 is adapted to emit at least two color lights. The color lights respectively correspond to different operating states of the radiography diagnosis device 100. For example, when the radiography diagnosis device 100 is turned on and operable, the light-emitting part 114 emits blue light, and during irradiation of the X-ray by the radiography diagnosis device 100, the light-emitting part 114 emits yellow light. Moreover, as shown in FIG. 1, the casing 110 of this embodiment may have an emergency stop button part 116 for the user to press in an urgent case where irradiation of the X-ray is required be stopped.

In summary of the foregoing, in the disclosure, the first shielding structure, the transmission-type X-ray source module, and the image receiving assembly are integrated into the same casing, different from the general radiography diagnosis system in which components such as the X-ray source device, the X-ray irradiation zone, and the image receiving device are separately disposed. Accordingly, the radiography diagnosis device of the disclosure is easily movable and occupies less space. Further, since the transmission-type X-ray source module of the disclosure has a greater light-emitting angle range than a reflection-type X-ray source, an overly long irradiation distance is not necessary for a sufficiently large irradiation area to be provided. Thereby, the distance between the transmission-type X-ray source module and the image receiving assembly (i.e., the source image distance (SID) as generally referred to) can be reduced. Moreover, the transmission-type X-ray source module of the disclosure has a lower wattage, and accordingly a smaller size, than the reflection-type X-ray source. Furthermore, in the disclosure, the duration of irradiation of the X-ray to the shielded space is controlled by the shutter assembly, and the light-emitting angle range of the X-ray is limited by the shutter assembly. The shutter assembly has a smaller size than other types of mechanical/electronic beam collimators. Therefore, in the disclosure, the miniaturization of the overall device volume is facilitated by using the transmission-type X-ray source module and the shutter assembly.

It will be apparent to those skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:

1. A radiography diagnosis device, comprising:
   a casing, having an opening;
   a first shielding structure, disposed in the casing and forming a shielded space, wherein the shielded space corresponds to the opening, and an object to be detected is adapted to enter the shielded space through the opening;
   a transmission-type X-ray source module, disposed in the casing and adapted to provide an X-ray to the object to be detected in the shielded space;
   an image receiving assembly, disposed in the casing, wherein the shielded space is located between the transmission-type X-ray source module and the image receiving assembly, and the image receiving assembly is adapted to receive the X-ray passing through the object to be detected; and
   a shutter assembly, wherein the shutter assembly is disposed in the casing and located between the transmission-type X-ray source module and the shielded space, the shutter assembly is adapted to control a duration of irradiation of the X-ray to the shielded space, and the shutter assembly is adapted to limit a light-emitting angle range of the X-ray.

2. The radiography diagnosis device according to claim 1, further comprising an image capturing device, wherein the image capturing device is disposed in the casing and corresponds to the shielded space, and the image capturing device is adapted to capture an image of the object to be detected in the shielded space.

3. The radiography diagnosis device according to claim 1, further comprising an electric transmission interface, wherein the electric transmission interface is disposed on the casing, and the radiography diagnosis device is adapted to receive power and transmit data through the electric transmission interface.

4. The radiography diagnosis device according to claim 1 further comprising a display interface, wherein the display interface is disposed on the casing and is adapted to display an image received by the image receiving assembly.

5. The radiography diagnosis device according to claim 1, wherein the casing has a transparent part, the transparent part corresponds to the shielded space, and the object to be detected in the shielded space is adapted to be observed through the transparent part.

6. The radiography diagnosis device according to claim 5, wherein a material of the transparent part comprises a shielding material.

7. The radiography diagnosis device according to claim 1, further comprising a dose measuring unit, wherein the dose measuring unit is disposed in the casing and is adjacent to the shielded space, and the dose measuring unit is adapted to measure a dose of the X-ray.

8. The radiography diagnosis device according to claim 1, further comprising a second shielding structure, wherein the second shielding structure is disposed in the casing and covers the transmission-type X-ray source module.

9. The radiography diagnosis device according to claim 1, wherein a bottom edge of the casing has at least one finger-receiving groove.

10. The radiography diagnosis device according to claim 1, wherein the casing has a light-emitting part, the light-emitting part is adapted to emit at least two color lights, and the color lights correspond to different operating states of the radiography diagnosis device.

11. The radiography diagnosis device according to claim 1, wherein the casing has an emergency stop button part.

\* \* \* \* \*